US007224362B2

(12) United States Patent
Kincaid et al.

(10) Patent No.: US 7,224,362 B2
(45) Date of Patent: May 29, 2007

(54) SYSTEMS AND METHODS FOR PROVIDING VISUALIZATION AND NETWORK DIAGRAMS

(75) Inventors: Robert Kincaid, Half Moon Bay, CA (US); David Moh, San Francisco, CA (US); Allan Kuchinsky, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 345 days.

(21) Appl. No.: 10/356,122

(22) Filed: Jan. 30, 2003

(65) Prior Publication Data
US 2004/0150644 A1 Aug. 5, 2004

(51) Int. Cl.
  *G06T 11/20* (2006.01)
  *G09G 5/00* (2006.01)
(52) U.S. Cl. ..................... 345/440; 345/629
(58) Field of Classification Search ............... 345/440, 345/441, 733, 734, 735–737, 629
See application file for complete search history.

(56) References Cited

U.S. PATENT DOCUMENTS

| 5,623,590 | A | * | 4/1997 | Becker et al. ............... 715/772 |
| 6,154,212 | A | * | 11/2000 | Eick et al. .................... 715/848 |
| 6,154,220 | A | * | 11/2000 | Prakriya et al. ............. 345/440 |
| 6,188,405 | B1 | | 2/2001 | Czerwinski et al. |
| 6,486,898 | B1 | | 11/2002 | Martino et al. |
| 6,646,652 | B2 | * | 11/2003 | Card et al. .................... 345/645 |
| 6,714,936 | B1 | * | 3/2004 | Nevin, III .................... 707/102 |
| 6,792,400 | B2 | * | 9/2004 | Alden et al. ................... 703/2 |
| 6,983,283 | B2 | * | 1/2006 | Sowizral et al. ............. 707/102 |
| 2002/0118214 | A1 | * | 8/2002 | Card et al. .................... 345/619 |
| 2002/0149602 | A1 | * | 10/2002 | Redpath et al. ............. 345/629 |
| 2002/0178184 | A1 | * | 11/2002 | Kuchinsky et al. ......... 707/512 |
| 2003/0011601 | A1 | * | 1/2003 | Itoh et al. .................... 345/440 |
| 2003/0020764 | A1 | * | 1/2003 | Germain et al. ............. 345/853 |
| 2003/0219149 | A1 | * | 11/2003 | Vailaya et al. .............. 382/128 |

OTHER PUBLICATIONS

Lamping, J., et al., "ACM: A Focus+Context Technique Based on Hyperbolic Geometry for Visualizing Large Hierarchies"; May 7, 1995 Human Factors in Computing Systems. CHI '95 Conference Proceedings, Denver, 05/ 7-11, 1995, Conference on Human Factors in Computing Systems, NY, ACM US pp. 401-408.
Partial European Search Report EP 04 25 0138.

\* cited by examiner

*Primary Examiner*—Ryan Yang

(57) ABSTRACT

Visualization techniques tools and systems for displaying network diagrams to convey both focus and context to a user of the display. Network diagrams may be displayed to emulate a three dimensional presentation. Network diagrams may be presented with items of interest in sharp definition and the remainder of a diagram or diagrams being blurred or having relative degrees of sharpness/blurriness.

15 Claims, 11 Drawing Sheets

SYSTEMS AND METHODS FOR PROVIDING VISUALIZATION AND NETWORK DIAGRAMS

FIELD OF THE INVENTION

The present invention relates to systems for visualizing data, and more particularly to displaying visualizations of network diagrams.

BACKGROUND OF THE INVENTION

Network diagrams (node-link graphs) have wide scope of applications in almost all domains of science. Any data set that can be modeled as a collection of linked nodes can be represented as a network diagram. In life science, a network diagram can be used as a pathway diagram, protein interaction diagram, signal transduction process, workflow process, and other similar processes. Network diagrams may be used to provide computer-based visualization of computer networks, communications networks, and many other technical systems.

Computer-based visualization of network diagrams involves contributions from many disciplines such as: graph theory, information visualization technology, visual perception, cognitive science, as well as others, to arrive at an efficient representation that exploits human visual processing to reduce the cognitive load of many tasks that require understanding of global or local structures.

While network diagrams may convey necessary information, many times they become more confusing than necessary. For example, in the case of biological diagrams, if a diagram is utilized to illustrate a pathway or interaction diagram, the amount of graphics displayed on the screen may be overwhelming to the user. Further still, by restraining the connecting lines to two dimensions, this may limit the ability of the program to display all connections in a logical or easily perceivable manner.

Many times one line may be drawn over another line, thereby making the diagram visually confusing to the user such that the user, must take time to trace the appropriate line across/down the screen in order to see the connection between the nodes.

Further, while network diagrams may be useful to display an amount of data in a more simplified graphical nature, there are still shortcomings when it is desirable to display more than one set of data at a time. For example, in gene expression, it may be desirable to display multiple tests on a single screen using a network diagram so that the user can determine if any data collected in each test differs in any manner, or to attempt to observe connections among the data. In order to make such diagram displays from which the observations can be made, data values are encoded and the encodings are used to render the network nodes and links, see, e.g., co-owned and currently pending application Ser. No. 10/155,616, filed May 22, 2002 and titled "System and Methods for Visualizing Diverse Biological Relationships", which is incorporated herein, in its entirety, by reference thereto. It would be desirable to overlay encoded values from other data sets on the nodes to make comparisons between values from different experiments with regard to the same entity represented by a given node. Conventional network diagrams cannot be utilized to display more than one data set because each data set will be written over the other one and/or some portions of each data set may be blocked by a portion of another data set.

Therefore there is a need for improved network diagrams and visualization techniques that can convey visual information to a user in a more simplified manner. There are further needs for providing visualization schemes capable of displaying more than one set of data simultaneously, while still providing easily interpreted readability.

An earlier attempt at presenting graphical detail in a more readable format is available in a product known as "Star Tree Viewer" (available from Inxight Software, Sunnyvale, Calif.), a screen display of which is shown in FIG. 9. Star Tree Viewer provides a technique whereby an entire tree can be kept within the confines of a circular area on a conventional display screen. The Star Tree Viewer renders a tree data structure onto a hyperbolic surface, with the higher level nodes displayed at the center of the display and "branches" of the tree extending radially outwardly therefrom toward the periphery to display lower level nodes, resulting in an appearance of the form shown in FIG. 9. Although Star Tree Viewer provides an interesting view of a hierarchical structure, it is only applicable to tree structures and not to network diagrams or graphs in general.

FIG. 10 shows a view of a product known as "Pop out Prism" (http://www2.parc.com/csl/projects/popoutprism), by Xerox Parc, which provides a Web browser that aids navigation by providing an enhanced thumbnail overview of Web pages. This enhanced thumbnail contains attention-grabbing "popouts" which are generated dynamically based on user input of URLs and keywords. These popouts enable users to immediately locate relevant information in a page. Popout Prism also adds popouts to full Web pages so that users can recognize and locate keywords. This scheme is only suited for textual images, not for graphs.

SUMMARY OF THE INVENTION

The present invention provides a system, methods and tools for displaying network diagrams in ways that are much easier for a user to visually interpret. Focus and context of information contained within one or more network diagrams may be displayed on a single display. According to one aspect of the present invention, nodes of interest, either selected explicitly by the user or implicitly by an algorithm, pop up, become bigger and/or brighter, and hence appear "closer" to the user than other nodes. This provides a way to distinguish these nodes from the rest of the network, and achieves a focus-and-context view, meaning the node of interested (the focus) is displayed in the backdrop of the rest of the network diagram (the context).

The contrast between the focus and the context can be further sharpened by either pushing the nodes in the context farther away, by displaying them smaller and dimmer, or by "fading" them, by displaying them in semi-transparent mode. Another interesting aspect of this feature is that the focus is not singular, and not of a single degree. More than one node can be in focus, and nodes can be in various degrees of focus.

Whenever a node is selected and in focus, all nodes that are connected directly to this node may be automatically set in a lower degree of focus, and nodes that are connected to these nodes are in turn set in focus of even lower degree, and so on. In other words, nodes are set in varying degrees of focus which correlate to the degree of their connection to the primary focus. This scheme provides an excellent way to highlight the connectivity of a node or a cluster of nodes, and allows the user to interactively traverse the network by clicking one node following another.

For application to large networks that necessarily contain hidden topology and/or structure (including semantic information), the present invention allows these hidden topologies/structures to be highlighted or displayed, by setting the relevant nodes in focus.

One difficult problem in network visualization is scaling. When a network contains more than a few hundred nodes, these nodes must be either drawn very small in order to be distinctive, or they are crowded together in a limited screen space overlapping one another. The overlapping of nodes is usually considered undesirable since it obscured the connectivity information. The present invention turns this obstacle into an asset by using the visual metaphor of 2.5D, namely the object "bigger and closer" should block objects "smaller and farther away". The term "2.5D" refers to "two and one half dimensions", to distinguish between two-dimensional visualizations and true three-dimensional visualizations. A two-dimensional ("2D") visualization is a flat, planar visualization, taking into account only planar geometry (x and y axes). A three-dimensional ("3D") visualization takes into account full 3-dimensional geometry, with continuous values on x, y, and z axes, and would be represented in terms of a solid object hologram, for example. A 2.5D visualization, as used here, is a "layered" geometry. The third dimension is not continuous, but is made up of a number of discrete "layers", such as the example given above of a larger object layer being laid over a smaller object layer. In this way, the partial blockage between objects produced by the overlapping (superimposing) gives the visual effect of "depth" making the visualization appear almost as a three dimensional image, and may be a visual clue as to the topology of the connectivity.

The present invention provides systems, methods and tools to represent data in a network diagram for facilitating visualization of relations between components of a network diagram and or comparison between network diagrams, where data from one source or view is superimposed upon data from a second source or view. The visualizations may further include additional visualization properties such as color, size, degree of sharpness or blurringfocus, shape, contrast, brightness and other similar tools and methods to enhance visualization.

The present invention provides a system that allows users to graphically display at least one data set showing connections and relations between the data of the data set. The present invention is also capable of providing visualization of network diagrams wherein one set of data may be overlaid over one or more additional data sets for direct comparison of data. Applications for visualizing the comparisons may be employed which allows a user to select a data point or node to be displayed, wherein visual aspects of related data will be altered in response to the user's selection.

In accordance with the present invention, it may be desirable to display data from various sources. For example, data may be contained within predefined network diagrams in databases accessible by the present invention, while additional sources of information may be accessed to provide overlays of annotations, or other related data to the network diagrams. Such additional information may be inputted from pre-sorted tables, text from articles, books or other publications, databases accessible through the internet or other databases, including proprietary databases, etc. Additionally, the user may manually enter data using an input device, such as a keyboard, mouse, scanner, data storage means such as a floppy disk, cd-rom and the like. The present invention also provides various methods of overlaying data from one or more data sets onto data from another data set, or vice versa. The overlay may be visualized to compare the data from the two or more sources. Further, a visual indicator may be provided on the data upon which the overlay is produced, to further facilitate the comparison of data.

The actual data from one data set may be overlaid on the actual data of another data set based on local formatting and linking of the same, to enable a literal comparison thereof.

Extraction of data from various categories may be performed automatically, semi-automatically or manually, for inputting the relevant data to a local format module for representation of the relevant data in the local format. The local format may take the form of a programming language, grammar or Boolean logic, for example.

Automatic comparison of the overlaid relevant data with the relevant data upon which it is overlaid may also be provided. Additionally, the user may be alerted when the means for automatically comparing determines there is a discrepancy found by the comparison.

Among other advantages, the present invention allows users to automatically overlay information on biological models and experimental data, including imported versions of each of these formats.

These and other objects, advantages, and features of the invention will be apparent to those persons skilled in the art upon reading the details of the invention as more fully described below.

DETAILED DESCRIPTION OF THE PREFERRED EMBODIMENTS

Figure 1A:
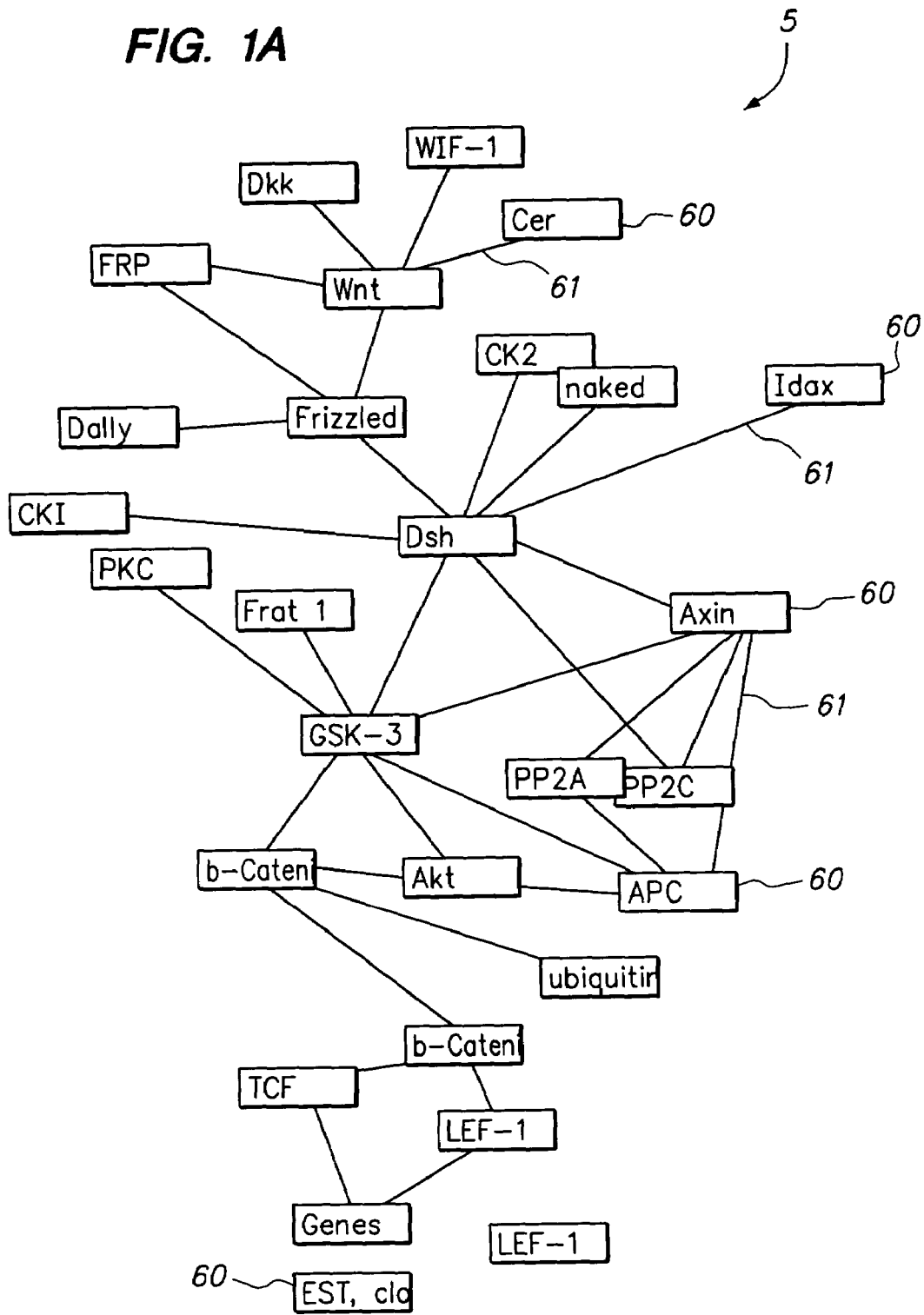
FIG. 1A shows an example of a visualization of a network diagram.

Before the present system, software, and methods are described, it is to we understood that this invention is not limited to particular data sets, types of data sets, commands or steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a step" includes a plurality of steps and reference to "the pathway" includes reference to one or more pathways and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dated which may need to be independently confirmed.

Interpretations/hypotheses which are developed in story or textual form or diagrammatic form may be dependent upon many different cellular processes, genes, and various expressions of genes with resultant variations in protein abundance. Correlation and testing of data against these hypotheses is becoming increasingly more tedious and lengthy with the increased automation of the ways in which gene and other data is generated (e.g. microarrays, mass spectroscopy, etc.). when viewed in the form of network diagrams or node-link graphs, the sheer abundance of this information can become overwhelming to the viewer, to the point where it is difficult to perceive useful data because of overcrowded displays, overlapping data, too much information displayed at a time, or other complications due to the complexity of the information that is being displayed. The present invention provides systems, tools and methods for visualizing data in network diagram (e.g., node-link) form, in manners that facilitate the visual interpretation by the user, wherein useful data may be more easily and readily distinguished.

The present invention facilitates visualization and comparison of data to validate/invalidate data and hypotheses, as well as develop new hypotheses/refine existing hypotheses, discover correlations, etc.

The present invention may also very useful to correlate experimental data with other representations of biological data, for example, correlating gene expression data with genes on a network diagram view, correlating sets of data pertaining to the same genes and relationships (or other nodes and links), correlating protein abundance data with proteins in a pathway diagram, etc.

The present invention addresses the ability of displaying information on a display device in a manner that a user perceives to be three-dimensional. Human beings live in a three-dimensional world, though human vision is primarily two dimensional in nature. The human retina can only register two-dimensional images, though through the use of both eyes, humans are able to utilize depth perception to process three-dimensional information. The distance between the eyes is so short that depth perception is limited, therefore it is difficult to distinguish the distances between various objects and the observer by depth perception alone. Since humans need to survive in a three-dimensional world, they have evolved highly efficient skills in using a number of visual cues to help us determine the third dimension. For example, if two objects share similar physical size and color, but one appears bigger and brighter that the other, the observer knows immediately that the former is closer than the latter. Processing of this kind of information is done in a subconscious and pre-attentive manner, because it is so common and because it is so important. Therefore it is an object of the present invention to provide a method and apparatus capable of utilizing these powerful human faculties to display items on a visual display device, wherein the items appear to be three-dimensional, thereby focusing a user's attention to specific information.

The present invention provides novel techniques and tools for exploring and navigating network diagrams. Referring to FIG. 1A, an example of a visualization of a network diagram is shown. Network diagram 5 includes a plurality of nodes 60, each of these nodes 60 configured to represent data, in this case biological data, such as gene-related data. Each node 60 is displayed on the display device 50 in the visualization of FIG. 1A, such that each node has the same or similar size, shape, and contrast, as is standard in network diagrams as they are currently produced. Each node 60 may include at least one line or link 61 extending therefrom and connecting to another node 60. Each link 61 is utilized to represent a connection or a relation between the nodes 60 that it interlinks, wherein the links may be displayed having the same weight and contrast. Generally, the relationship between the nodes 60 is known, for example, in gene expression experiments, relations between genes and gene expression values for a given experiment may be known. The known relationships are inputted as data characterizing the nodes when the node data is inputted, and the relation data is utilized to draw the connection lines 61.

If a relationship is not known, a link 61 cannot be generated for such a node, the node may be displayed, but with no connecting links, as in the case of node "EST,clo" 60, to indicate that no links exist (no relationships) between the other nodes shown has yet been established). During the course of investigation and study of this data, a user may discover a relationship and manually input a connecting link, for example, in the same manner as the links are shown connecting other nodes. For more information on the input and display of network diagrams, the reader is referred to co-pending, commonly owned U.S. application Ser. No. 10/155,616 titled "System and Methods for Visualizing Diverse Biological Relationships", filed on May 22, 2002; co-pending, commonly owned U.S. application Ser. No. 10/155,615 titled "System and Methods for Extracting Semantics From Images", filed on May 22, 2002; and co-pending, commonly owned U.S. application Ser. No. 10/155,304 titled "System, Tools and Methods to Facilitate Identification and Organization of New Information Based on Context of User's Existing Information", filed on May 22, 2002. Each of these applications is incorporated herein, by reference thereto, in its entirety.

As can be seen in FIG. 1A, some of the data displayed is already beginning to overlap and crowd one another even though this example is a fairly simple one and most real diagrams contain numbers of nodes and links which are orders of magnitude higher than shown here. For example, the "PP2A" and "PP2C" nodes are overlapping somewhat in the view of FIG. 1A. Additionally, when all nodes and links are displayed equally, or in the same fashion, it can be considerably difficult to trace out all of the interrelationships between a node or nodes of interest and those nodes that are interlinked. This difficulty only increases as the number of nodes and links displayed increases. If one or more nodes or links are overlapping, it may not even be possible to accurately identify all of the interlinks of interest.

Figure 2:
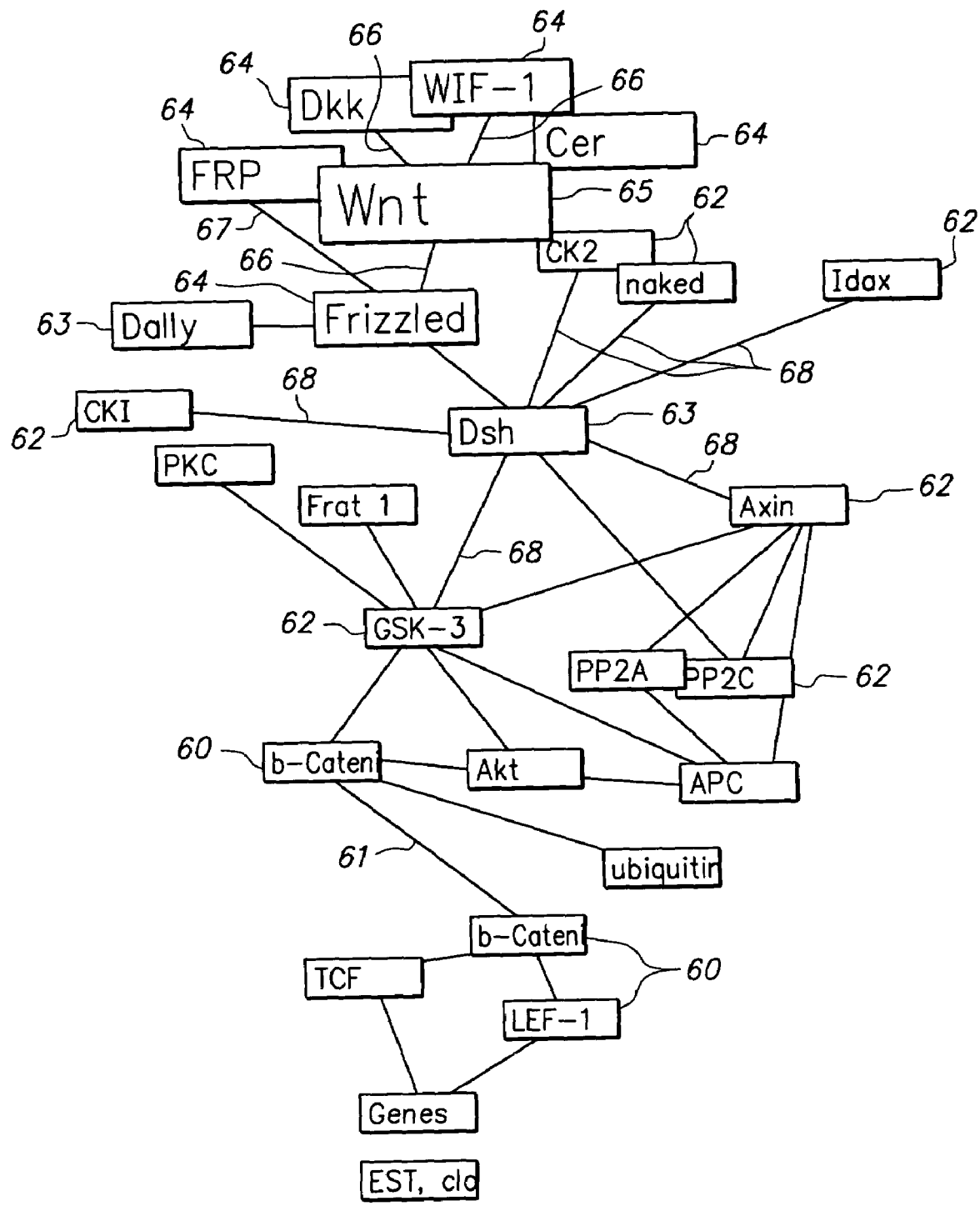
FIG. 2 shows an example of a visualization of the same network diagram displayed in FIG. 1A, as modified according to an aspect of the present invention.

FIG. 2 shows an example of a visualization of the same network diagram 5 displayed in FIG. 1A, as modified according to an aspect of the present invention. In this visualization, the user is particularly interested in investigating the properties and relationships characterizing the node "Wnt" 60. A node or node of interest may be explicitly selected by a user, such as by "selecting" the node by hovering a cursor over it and clicking with a mouse or selecting with keyboard input, or implicitly by an algorithm. As to selecting by algorithm, a user may search for all nodes whose names begin with the letter "W", for example, and all nodes that fit this description (e.g., nodes "Wnt" and "WIF-1" in the example of FIG. 1A) will be selected.

In the view shown in FIG. 2, by selecting the "Wnt" node, the system enlarges the representation of "Wnt" node 60 so as to be prominently displayed in the visualization as the largest sized node 65, as shown in FIG. 2. Additionally, node 65 is displayed with the greatest brightness or intensity relative to all other nodes in the display. Nodes 60 which are directly connected to node 65 are also displayed larger relative to the size of nodes 60 as nodes 64. The size of a node 64 is smaller than the size of node 65, however, so that the node (or nodes) of interest are still displayed the most prominently. Likewise, nodes 64 are displayed brighter than nodes 60, but not as bright as node 65. Also, in circumstances where nodes or links overlap due to the enlargement of the visualization, node 65 is displayed on top, as shown in FIG. 2.

The example of FIG. 2 shows four levels of modified node sizes and brightnesses. That is, any node 60 which is interlinked with one or more nodes 64 is displayed larger and brighter than nodes 60 as a node 63, which is not as large or bright as node 64. Also, any node 60 which is linked to one or more nodes 63 is displayed larger and brighter than nodes 60 as a node 62, which is not as large or bright as node 63. The remainder of the nodes 60 are maintained as is, with a size and intensity the same as displayed in FIG. 1A. It should be noted here that the example display that differentially displays four levels of nodes is an example only and is not to be limiting, as more or fewer levels of nodes may be differentially displayed depending upon the complexity of the diagram that is being displayed, and the user's particular interests, among other factors. is displayed larger and brighter than nodes 60 as a node 63, which is not as larger or bright as node 64.

Additionally, links 61 which interconnect the levels of differentially displayed nodes 65, 64, 63, 62 may be differentially expressed. For example, links interconnecting nodes 65 and 64 may be displayed as the largest (thickest) and brightest links 66 on the diagram. Links connecting with one or more nodes 64 but not a node 65 may be displayed as links 67, which are thicker and brighter than links 61, but not as thick or bright as links 66. Likewise, links connecting with one or more nodes 63 but not a node 64 may be displayed as links 68, which are thicker and brighter than links 61, but not as thick or bright as links 67. The same rules for displaying the differentially sized links may apply as with respect to the differentially sized nodes, described above. That is, the largest size is displayed on top, followed by the next smaller size, and so forth. After the user has selected one or more nodes, the display is cleared and then redisplayed, with the selected node(s) and optionally, related nodes, drawn with the larger size assignments and changed color/contrast assignments.

As shown in FIG. 2, the increase of size and brightness of the selected node, as well as the increased size and brightness of the related nodes creates a visual effect, wherein the selected node and the related node(s) appear to float above or be projected above the remaining nodes. Thus, the selected node and the related nodes will appear to be displayed three dimensionally. By varying the sizes of the nodes (and, optionally, the links) and/or brightness as shown in FIG. 2, a user is able to more readily and more easily see the levels of connection between the selected node(s) 65, those nodes 64 which are directly linked to node(s) 65, and nodes which are indirectly linked to node(s) 65, but linked more closely than the general population of nodes displayed, as the nodes of interest appear larger and closer to the viewer. For example, nodes 62 have a size smaller and dimmer than nodes 63–65 but larger and brighter than the remaining nodes 60, which visually indicates to the user that these nodes 62 are connected to the selected node 65 through three related connections instead of a direct connection. From this, the user may be able to conclude that nodes 62 are related closely enough to node 65 to be of interest in an interaction that is being studied.

Figure 3:
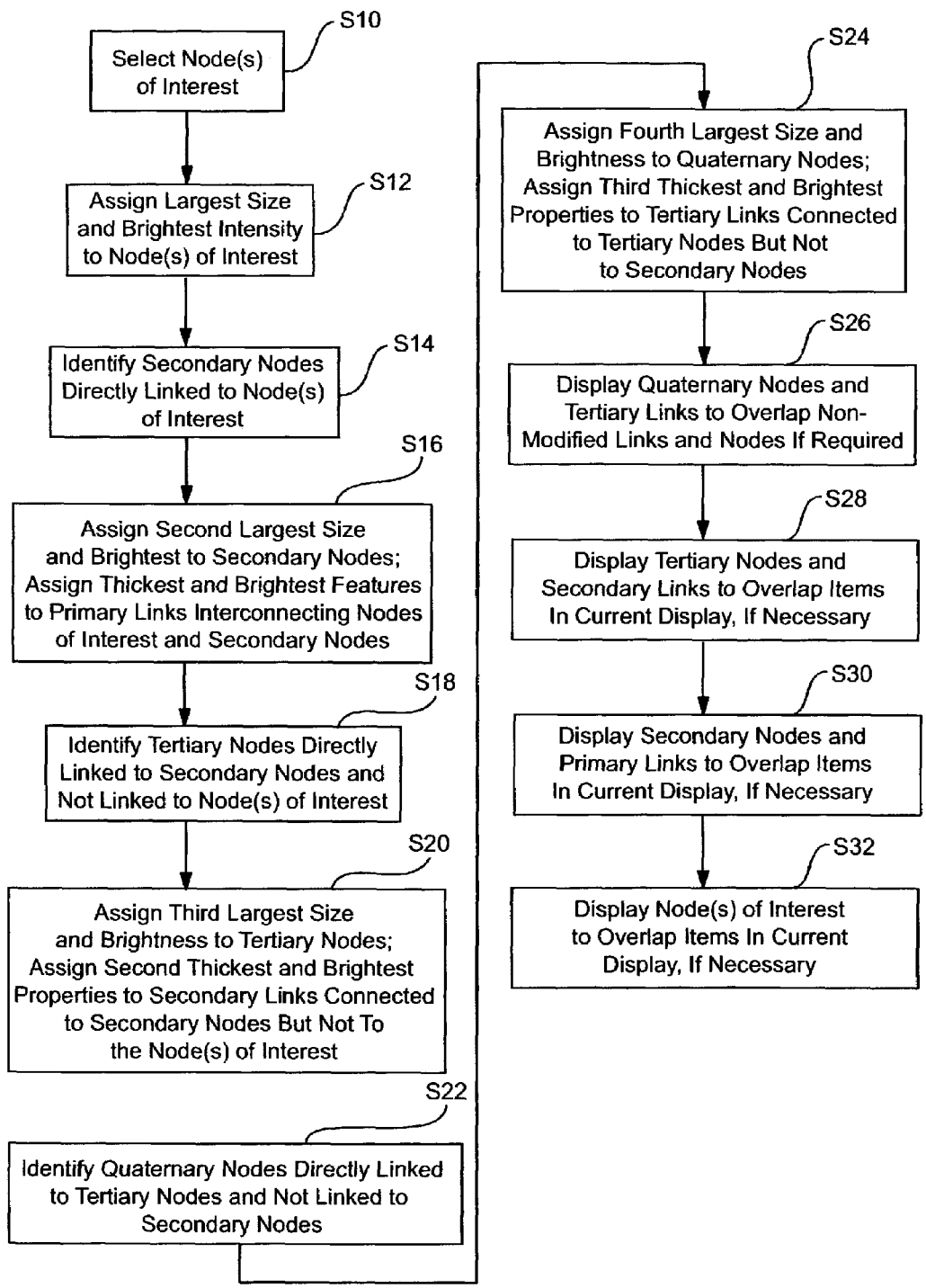
FIG. 3 shows a flowchart which refers to the processing of nodes and links upon selection of one or more nodes of interest.

FIG. 3 shows a flowchart which refers to the processing of the nodes 60 and links 61 upon selection of one or more nodes of interest, whether the selection is performed manually by the user, or according to an automated algorithm which selects a node or nodes of interest based on inputted properties which are desired to be studied by the user. At step S10 a selection of one or more nodes 60 of interest is identified. The one or more nodes of interest is assigned the largest size and (optionally) the brightest intensity at step S12. The system then identifies secondary nodes at step S14 by identify links 61 leading from the node(s) of interest and determining which nodes links 61 connect with. Secondary nodes are assigned the second largest size (and intensity) at step S16 according to the arrangement described above. Even when using a schema to vary four levels of nodes, the sizes used for the four levels may be adjustable, such as by the provision of a magnification slider, for example, so that the user can amplify select levels by an amount that best fits the application. Optionally, the links 61 joining the node(s) of interest and the secondary nodes are assigned the largest thickness and/or brightness.

At step S18 tertiary nodes are identified by those nodes which are directly linked to the secondary nodes and which are not linked directly to a node of interest. The third largest size (and intensity) are then assigned to the tertiary nodes at step S20 and optionally, the second thickest and brightest properties are assigned to secondary links, which connect secondary nodes with tertiary nodes.

In like manner, quaternary nodes are identified at step S22 by identifying those nodes which are directly linked to the tertiary nodes and which are not linked directly to a secondary node. The fourth largest size (and intensity) are then assigned to the quaternary nodes at step S24 and optionally, the third thickest and brightest properties are assigned to tertiary links, which connect tertiary nodes with quaternary nodes.

At step S26, the standard visualization (like that shown in FIG. 1A, for example) is modified by displaying quaternary nodes and tertiary links according to their newly assigned size/brightness characteristics. If the larger sizes interfere with the positioning of any of the nodes or links which have not been altered, the altered or larger sized nodes are overlapped on the non-altered nodes and links in the areas of interference.

At step S28, the tertiary nodes and secondary links are displayed according to their newly assigned sizes/brightnesses. Tertiary nodes are displayed over quaternary nodes, tertiary links, or unaltered links or nodes where interference occurs.

By a similar process, secondary nodes and primary links are displayed at step S30, ending with a display of the node(s) of interest at step S32, which is/are displayed so as to overlay any other interfering node or link of the visualization, resulting in a visualization as shown in FIG. 2.

Figure 4:
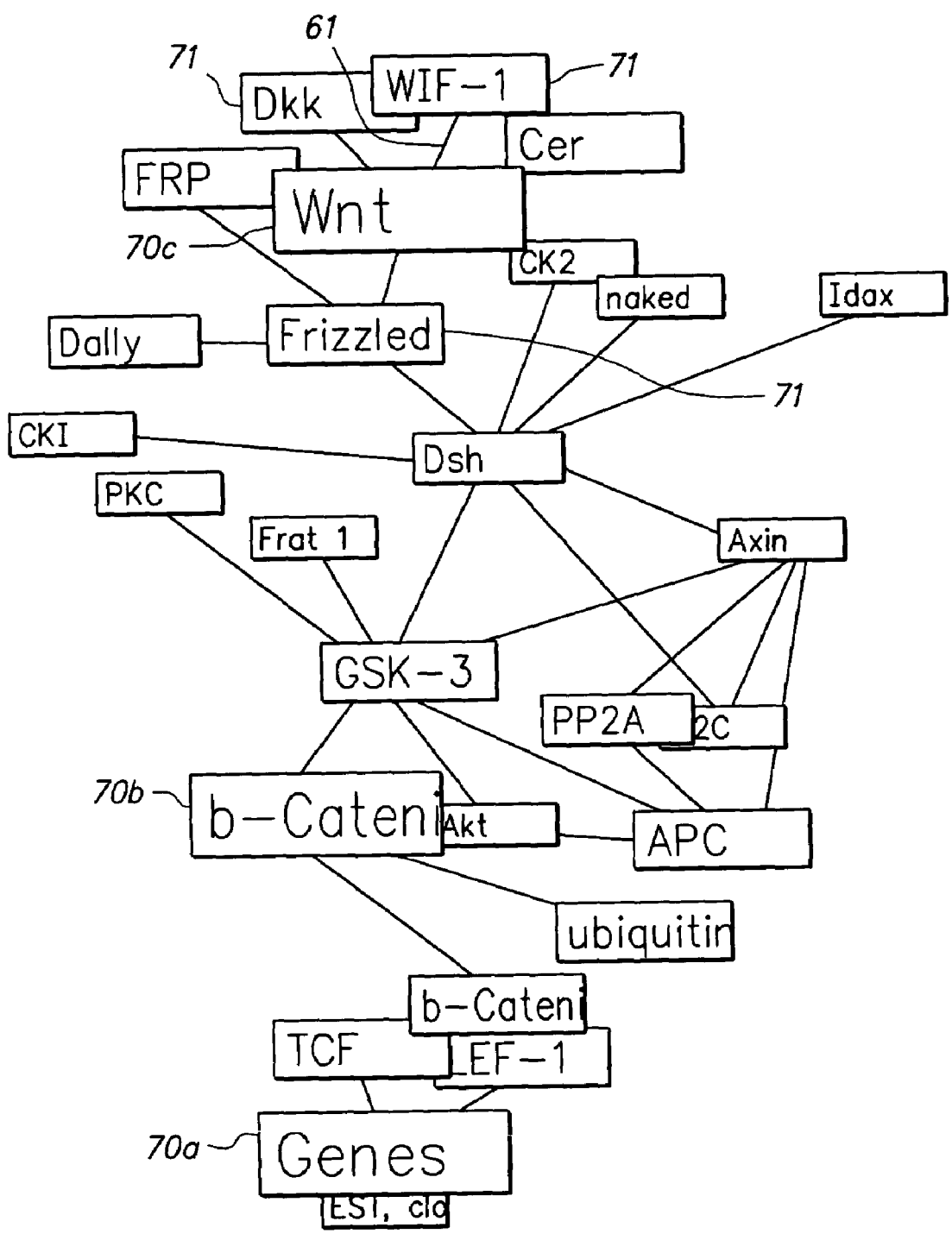
FIG. 4 shows an exemplary screen shot of a network diagram display in accordance with the present invention.

Referring now to FIG. 4, there is shown an exemplary screen shot of a network diagram 5 in accordance with the present invention, wherein the user has selected more than one node, either manually or by use of an automated algorithm. As shown in FIG. 4, nodes 70A, 70B, and 70C are shown to be larger in size and brightness than the remaining nodes, thereby indicating that a user has selected these nodes. Related nodes such as nodes 71 are also shown to have been increased in size and brightness, thereby enabling a user to more easily determine the relations between the closely related nodes and the selected nodes. Although not shown, it is contemplated that each node selected by the user in a manner described above, in addition to or in lieu of, may be displayed having a color or patterning that is different than the remaining nodes, thereby providing a visual effect to indicate that the node has been selected. Further still, if the user desires to chose more than one node, as shown in FIG. 4, each node selected may be displayed having a different color, thereby enabling a user to more easily determine related nodes. The color or patterning of the nodes may be automatically assigned to each node or group of nodes when the nodes are displayed on the display device. Alternatively, the user may input additional data that specifies a specific color or patterning for each node or sets of nodes.

The geometry of a selected node and related nodes may also be changed in the display to further emphasize the nodes of interest. For example, upon selection of a node as described above, the shape of the node may be changed from a rectangular box to another geometric shape such as an oval, rectangle, circle or other shape. The geometric shape of the nodes may be automatically assigned to each node or group of nodes when the nodes are displayed on the display device. Alternatively, the user may input additional data that specifies a specific shape for each node or sets of nodes.

According to the above arrangements, nodes of interest which are either selected explicitly by the user or implicitly by an algorithm, will "pop up", become bigger and brighter, and hence appear "closer" to the user than other nodes. This provides a way to distinguish these nodes from the rest of the network, and achieves a focus-and-context view, meaning that the node or nodes of interested (the focus) is displayed relative to the backdrop of the rest of the diagram (the context). Additionally, the contrast between the focus and the context can be further sharpened by either pushing the nodes in the context farther away, by displaying them smaller and dimmer, or by "fading" them, by displaying them in semi-transparent mode. Another interesting aspect of this feature is that the focus is not singular, and not of a single degree. More than one node can be in focus, and nodes can be in various degrees of focus.

As noted, nodes may be set in various degree of focus correlating to the degree of their connection to the primary focus (selected node or nodes). This scheme provides an excellent way to highlight the connectivity of a node or a cluster of nodes, and allows the user to interactively traverse the network by clicking one node following another.

Figure 1B:
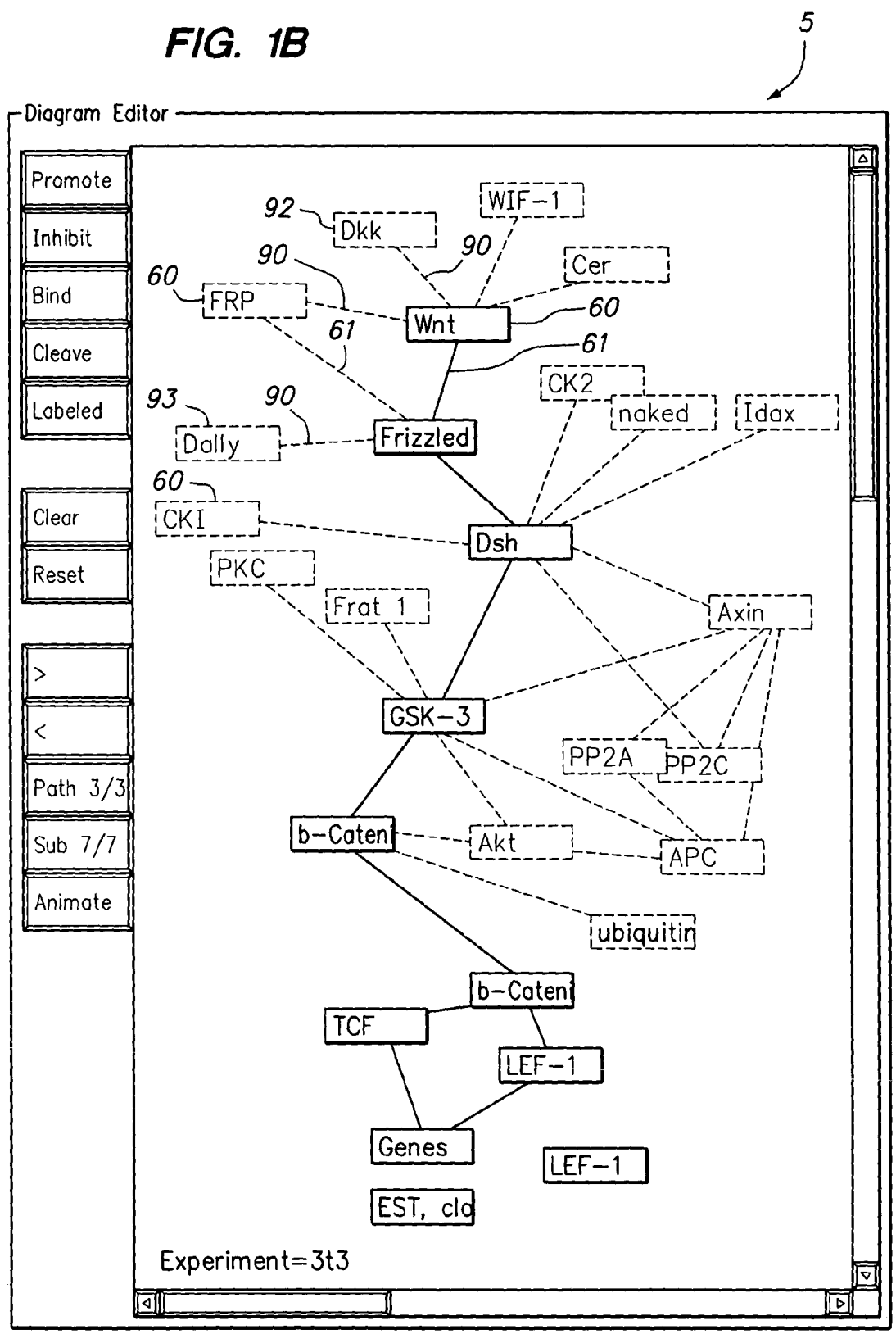
FIG. 1B shows a subpath through the pathway shown in the network diagram of FIG. 1A.

A large network may have topology (such as clusters or hubs) or other structures which are not visually apparent. Also, a network can contain semantic information that is not reflected in the connectivity itself. As another example, there may be paths through PPI (i.e., Protein-Protein Interaction) networks that are analogous to signal transduction pathways. The present invention allows these hidden structures in a network to be highlighted, by setting the relevant nodes in focus. For example, FIG. 1B shows a subpath (including nodes 92 and 93) through the wnt/beta-catenin pathway previously shown and described with regard to FIG. 1A.

One difficult problem in network visualization is scaling. When a network contains more than a few hundred nodes, these nodes must be either drawn very small in order to be distinctive, or they are crowded together in a limited screen space overlapping one another. The overlapping of nodes is usually considered undesirable since it obscured the connectivity information. The present invention turns this obstacle into an asset by using the visual metaphor of 2.5D, namely the object "bigger and closer" should block objects "smaller and farther away". In other words, the partial blockage between objects can be a visual clue as to the topology of the connectivity.

As a further modification to the visualization schemes described above, the remaining nodes (and, optionally, links), i.e., those nodes (and links) that have not been altered as to size or intensity, and which can be considered not closely related to the node(s) of interest, may be blurred so as to give the perception of a greater depth between the selected/related nodes and the non-selected/non-related nodes. Blur can be used as an alternative or supplement to the 2.5D effect of fading color to imply moving a node into the background. In this way, blur implies effects similar to photographic "depth-of-field". Viewers of such diagrams will intuitively interpret blurred, overlapped elements as being behind and less important than those sharply defined and in front.

Figure 5:
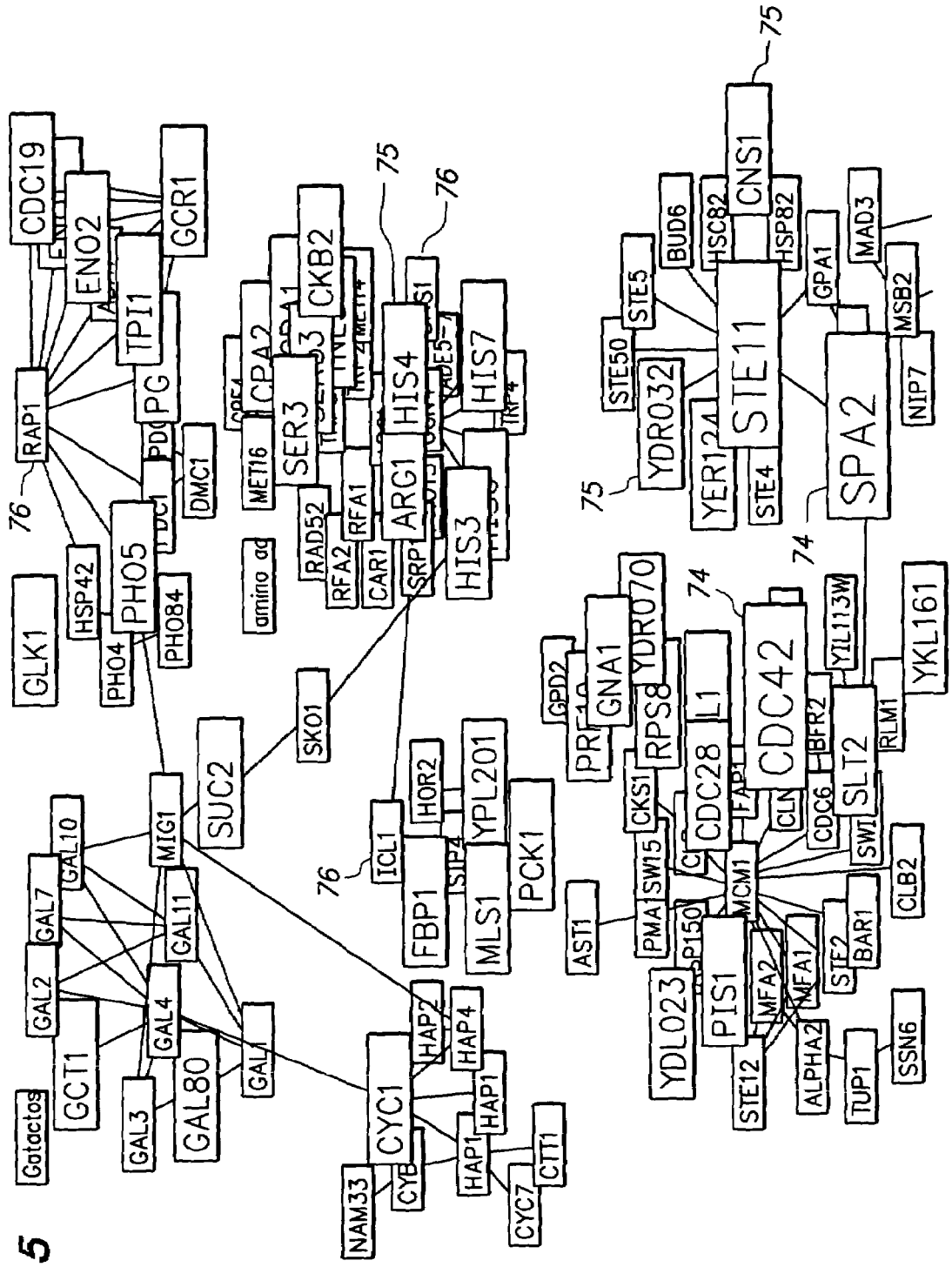
FIG. 5 shows an exemplary screen shot of a network diagram display in accordance with the present invention, in which non-selected nodes have been faded into the background of the display.

The blurring may be accomplished in any number of ways. For example, the sharpness of the nodes may be changed, the nodes may be pixilated, the brightness of the node may be reduced or the node(s) may be turned transparent so that they blend into the background. An example of nodes which have been "turned transparent" or "faded into the background" of the display is shown in FIG. 5, which shows three selected nodes 74 that are displayed in large size and high intensity brightness, with secondary nodes 75 shown in slightly lesser size and intensity. The remaining nodes 76 are faded, so as to blend in more with the background of the display. This has the effect of exaggerating the depth illusion of the visualization, thereby emphasizing the nodes of interest 74 and the secondary nodes 75.

Further still, whenever a node is selected, all nodes that are connected, i.e. through links 61, to a selected node may be automatically set to a lower degree of sharpness or clarity than that of the selected node(s), and tertiary nodes may be in turn set to a relatively lower level of sharpness (i.e., increased blurring) compared to the level of sharpness of the secondary nodes, and so forth. This process of stepping the sharpness/blurriness of the nodes will continue until the last layer of connected nodes is reached, or until a predetermined layer is reached. As discussed above, the present invention may be directed to affect nodes to a certain layer or level of connection, such as four layers from the selected node's layer. By varying the sharpness of each level of nodes, this further enhances the user's ability to readily visually determine the degree of separation of a given node from a selected node.

Figure 6:
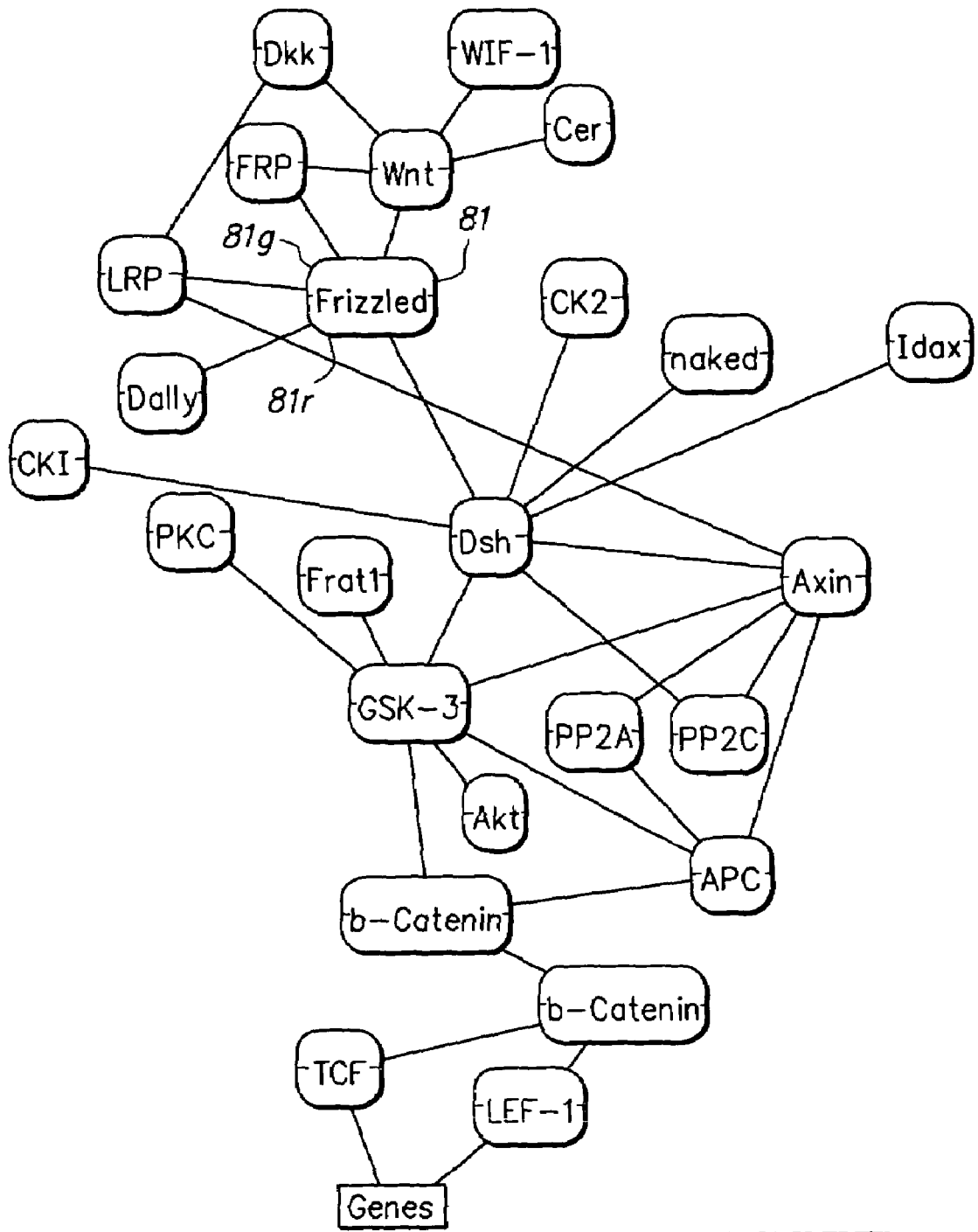
FIG. 6 shows the results of an ineffective effort to overlay gene expression data from two different experiments onto a pathway or interaction diagram.

Overlaying data representations on various visual representations presents many challenges. For example, FIG. 6 shows an effort to overlay gene expression data from two different experiments onto a pathway or interaction diagram. The gene expression data is color-coded according to a color scheme commonly used in heat map representations of expression data, i.e., wherein various shades of red coloring indicate varying degrees of up-regulation and various shades of green coloring represent various degrees of down-regulation. When the node corresponding to data from one experiment are overlaid directly on top of the other as shown in FIG. 6, the resulting visualization is very confusing and difficult to interpret, as any correlations between the coloring of molecules is disrupted by the differences in color between the two experiments being simultaneously overlaid. For example, node 81 ("Frizzled") is displayed as some mixture of green 81g and red 81r. Many other nodes suffer the same confusing appearance, making it difficult to draw any definitive conclusions from the display. The classic way to resolve the confusion created by such a visualization would be to create two separate graphs, each corresponding to a single experiment. However, this approach reduces the user's ability to compare trends within individual molecules as the user is forced to refer back and forth to two different graphs, which are not superimposed.

Figure 7:
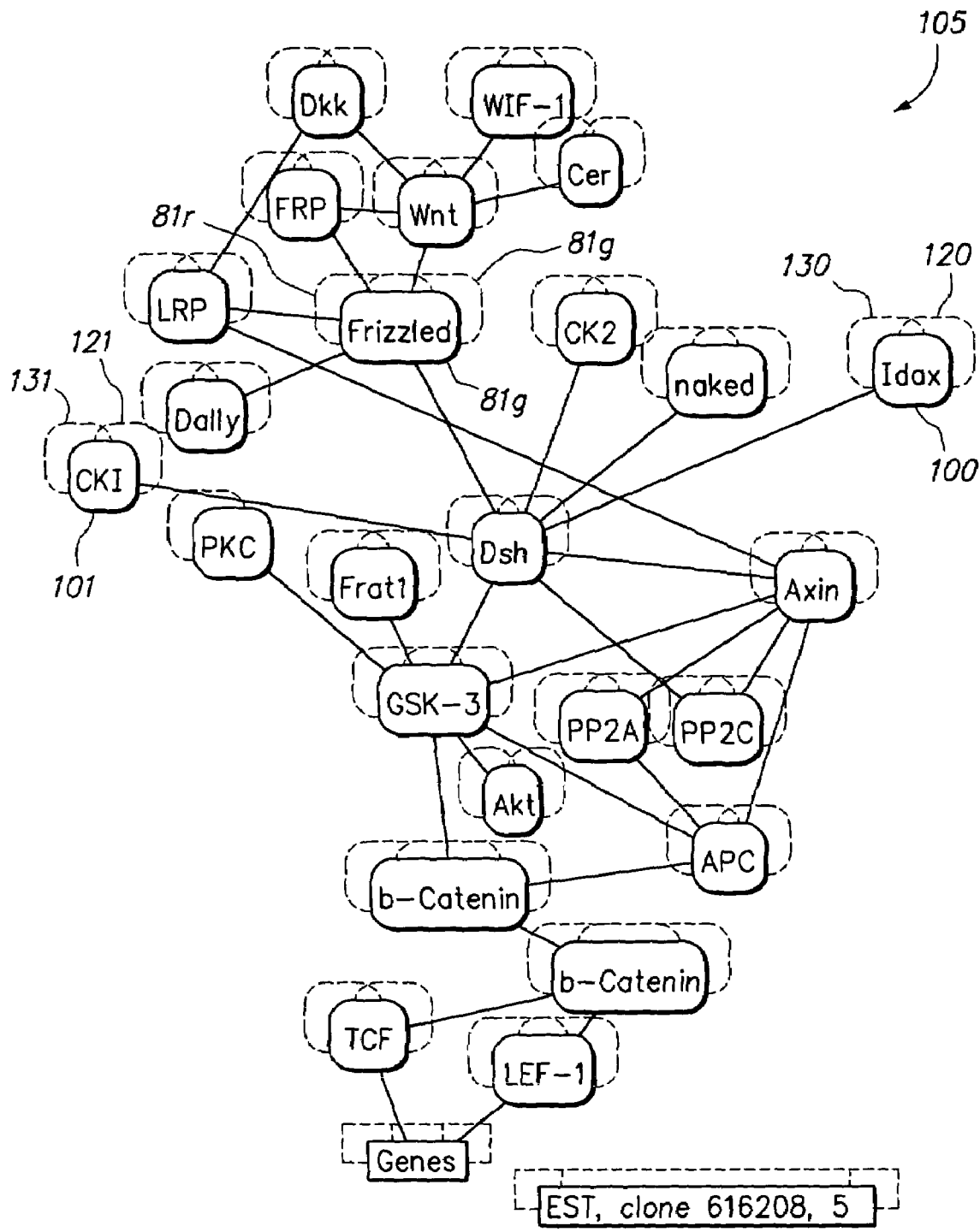
FIG. 7 shows the results of an example of an approach according to the present invention, of preparing a visualization similar to that shown in FIG. 6, but in which three experiments have been overlaid, in a manner which is more easily interpreted.

FIG. 7 shows an example of an approach according to the present invention, in which the visualization similar to that shown in FIG. 6, but in which three experiments have been overlaid, has been modified as visualization 105. The data from the three experiments are all displayed as superimposed graphs, except that all but one of the graphs is displayed in a visually diminished state so that it disrupts the overall pattern (and coloring thereof) less. In this instance, by clearly visualizing only one of the experiments and render the values from the other two experiments as blurred "shadows" that underlie the diagram of interest, the values in the sharp diagram can be readily ascertained. The diagrams are offset by a default amount, which may be adjustable by the user, to position the blurred diagrams in such a way that they resemble "drop shadows", as shown in FIG. 7. Providing a slight overlap, as shown, may be useful in facilitating comparison of the diagrams, making it easier for the user to find areas of disagreement between the diagrams, but is not required. In general the display may be adjustable by the user to allow for optimum viewing for the user's aesthetics. Diagrams may be uniformly distributed (e.g., "fanned out") to accommodate the display of more than three data sets.

In the example of FIG. 7, the sharp value for the node "Frizzled" now appears plainly and solidly as a green value 81g. However, the blurred values maintain their color-encoding (although with less intensity) and can be readily compared, with one of the values appearing as red 81r and the other being a green value 81g. In this way, the user can easily view and compare the overlaid values of the three experiments. Note that a combination of three experiments in the style of FIG. 6 would have appeared as an extremely confusing visualization and would have been virtually useless for comparing expression values, while in FIG. 7, the overall trend of the primary diagram is easily seen. However, the user can still inspect individual nodes of the graph to see behavior across the three experiments.

As shown in FIG. 7, a first data set 100 is visualized with sharp definition (i.e., sharply), while second and third data sets 120 and 130 are visualized as "blurred", although both the color and locations of the components of the second and third datasets 120,130 can still be viewed. The visualization of only a single data set in sharp definition, while diffusing or blurring the remaining data sets allows a user to compare more than one data set without disrupting the ability to visually parse trends within the sharp data of a single data set. For example, the data sets represented in the node diagram of FIG. 5 may be gene expression test results, wherein the sharp data set 100 is a control test to which the remaining data sets are to be compared. By sharply displaying the primary data set and overlaying this data set over the remaining data sets, a user can quickly determine if any data in the other data sets displayed is different than that of the primary data set through the use of color, geometry, shading or similar methods. For example, referring to sharp node 101 of FIG. 7, node 101 maybe represented on the visual display as having a green color. Nodes 121 and 131, representing the blurred data sets, may be assigned the color green if the data is similar to that of the sharp data set, or alternatively, if the data is not similar, the blurred data may be represented by a different color. Although the blurred nodes may not be readable, the visual attribute of a different color would be readily apparent to a user.

The data set that is displayed sharply may be changed by input from the user, for example. Such a change may be initiated by input through a mouse or keyboard, such as by positioning a cursor over one of the blurred data sets and selecting, or by use of a menu selection, or the like, to automatically display the selected data set with sharp definition and blur the previously sharp data set.

Figure 8:
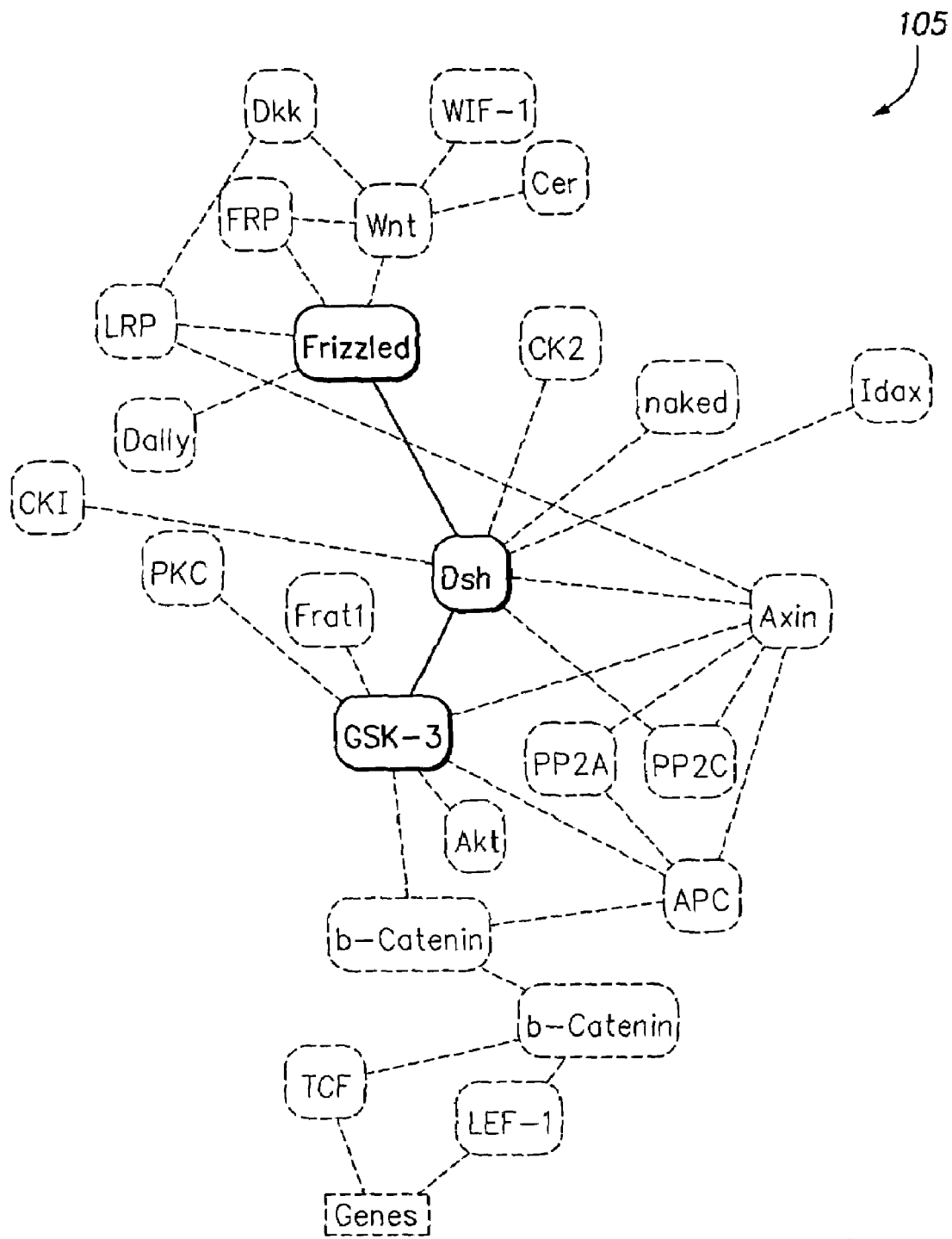
FIG. 8 shows a visualization of a the network diagram, according to the present invention, in which a sharpness/blur technique has been used to highlight a sub-path of a pathway diagram.
Figure 9:
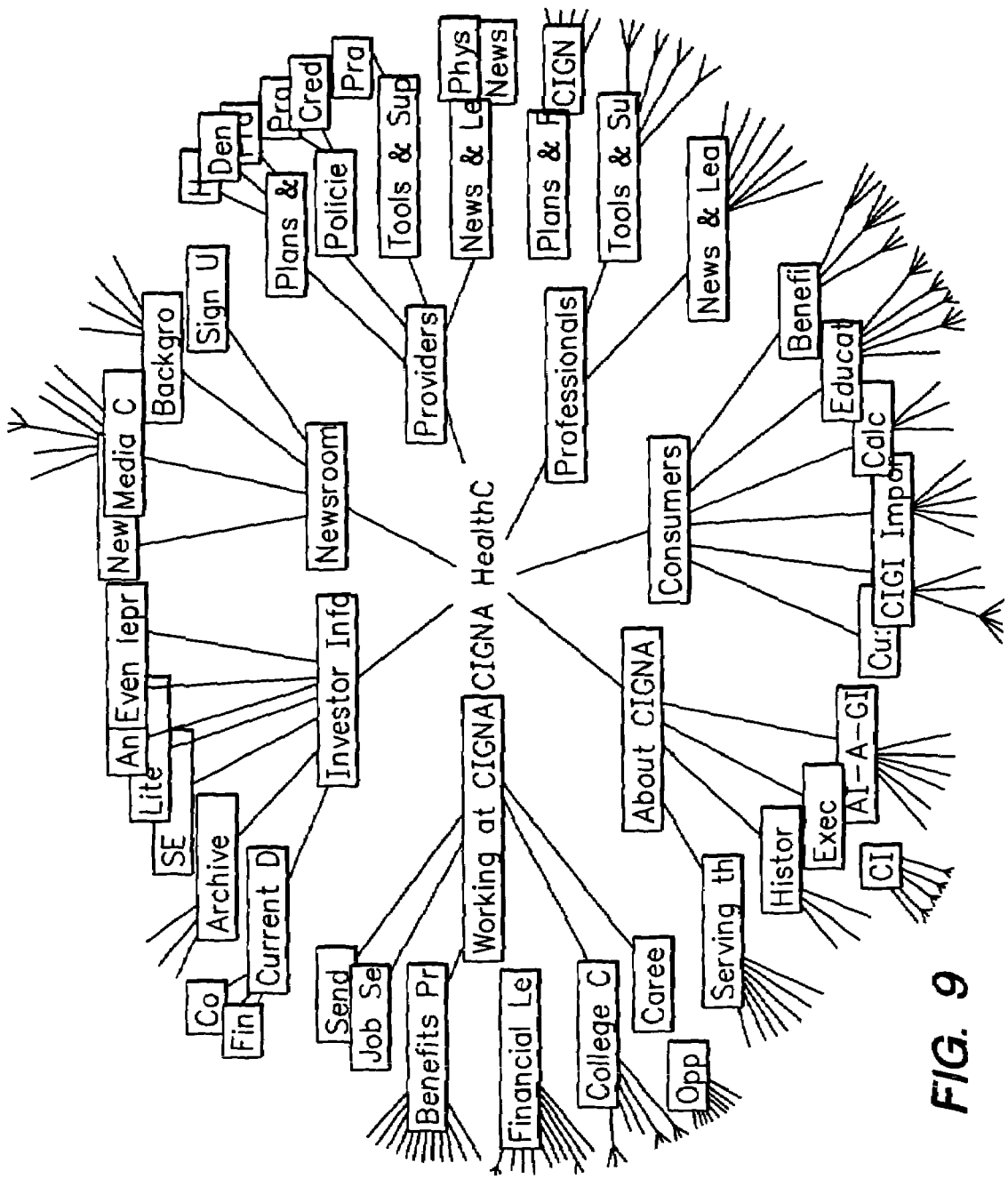
FIG. 9 shows a screen display of a prior art technique for visualizing tree diagrams.
Figure 10:
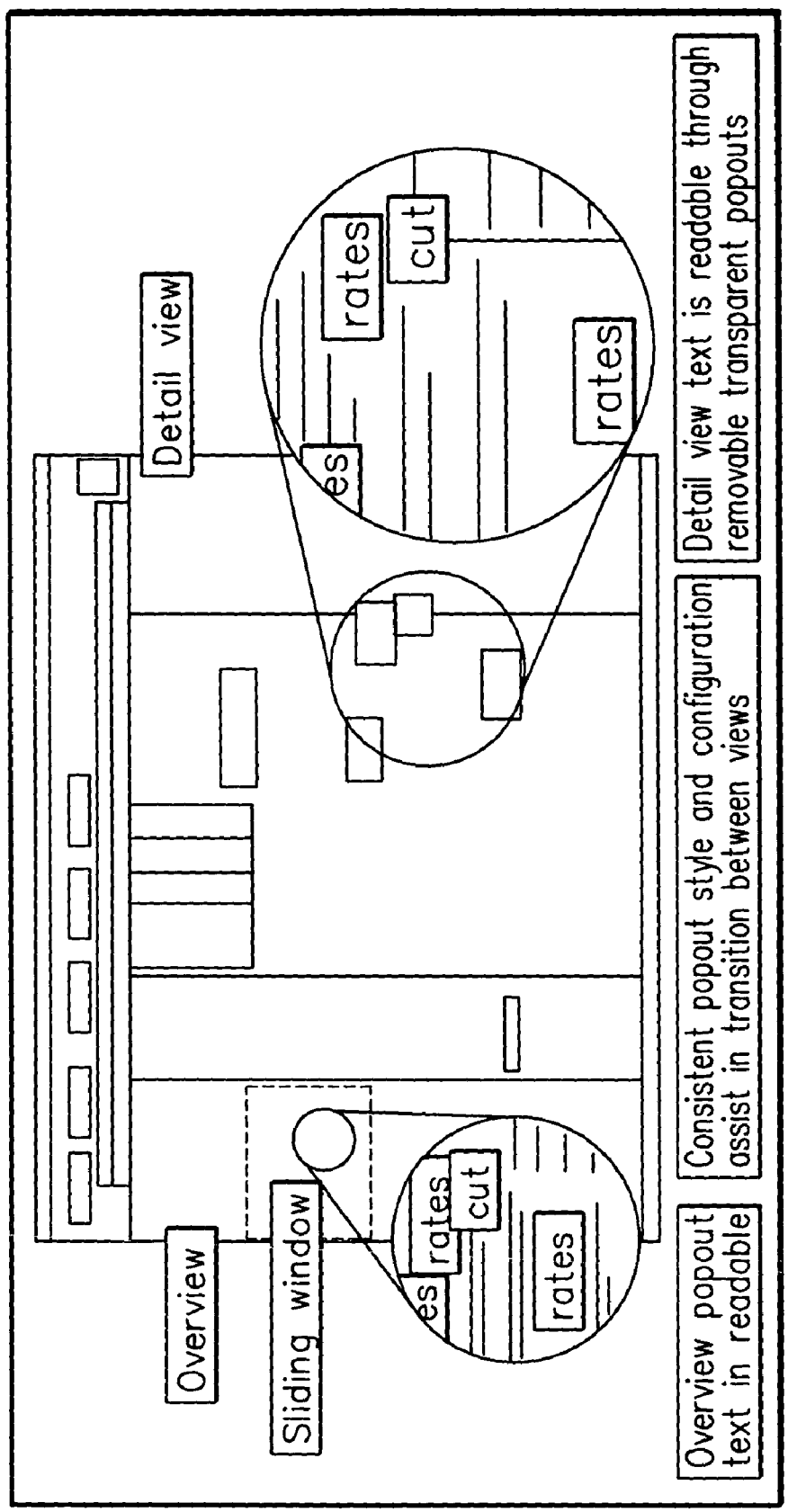
FIG. 10 shows a screen display of a prior art Web browser that aids navigation by providing an enhanced thumbnail overview of Web pages.

Referring now to FIG. 8, the network diagram 105 from FIG. 7 is shown wherein the sharp definition/blur technique has been used to highlight a subpath of a pathway diagram. Such a visualization may be accomplished by selecting multiple nodes, or through the use of an interface element that allows selecting a subpath, such as a sub-network, like the example described with regard to FIG. 1B above. Node(s) to be displayed in focus may be selected in the manner as described above, wherein the selected nodes may be enlarged in size and brightness in response to the user's input, the size and brightness may be pre-determined or selected through additional user input. As shown in FIG. 8, even the sharp data set may be partially obscured or blurred, for example, the non-selected or non-related nodes, e.g., nodes not directly linked to the selected nodes, may be blurred. In this view, the only nodes displayed sharply are those selected by the user and/or those that are directly linked to the selected nodes, thereby providing focus upon the selected nodes and potentially the nodes that are directly linked to the selected nodes. As in previous examples, this visualization may also be modified to show levels of connectedness or relativity. For example, two or more levels of relationship may be displayed in focus, or with varying levels of focus.

The process of enlarging and brightening the selected node(s) and the related nodes is similar to that described above. The related nodes may be displayed to produce a layering effect, wherein the selected nodes are largest and brightest, the most directly connected nodes are slightly smaller and less bright, the next level of relationship (those nodes that are connected to directly connected nodes) are slightly smaller and less bright, and so forth. The size and brightness of the nodes may be changed to pre-determined values, or the user may be prompted to enter desired values. The color and/or the geometric shape of the nodes may be changed to further distinguish the selected and/or related nodes from the remaining nodes, wherein the color and shape may be a pre-determined value or a value chosen through additional user input.

The level of sharpness of the visualization may also be utilized to convey characterizations of other information. For example, the user may choose a parameter of which the level of sharpness is to display. That is, the user may choose the level of sharpness to represent a parameter such as the standard of deviation, wherein this may be displayed on the display device by varying the sharpness of the data sets. For example, one of the data sets will be held in sharp definition and the remaining data sets will be diffused, the amount of diffusion indicates the standard of deviation of the remaining data sets from the sharp data set, thereby allowing a user to visually compare the data sets. Furthermore, this scheme may be applied at the individual node level, where those nodes in the blurred sets which have values within a defined standard of deviation value will be shown in relatively greater sharpness than those nodes outside of the defined standard. Alternatively, a continuous scale of sharpness/blurring may be employed relative to the standard of deviation, by which each node may be defined in a manner analogous to highlighting cells in a heat map view of gene expression data. This technique could be used in a binary way to indicate selections or regions of interest. Thus, the degree of blur or sharpness may be utilized as an indicator of experimental uncertainty. For example, those nodes having measurements with relatively high p-values or high standard deviations may show relatively more blurring, while those with relatively low error statistics may be displayed as relatively sharp. Such a visualization will intuitively imply to the user the data that is well characterized (i.e., relatively sharp) vs. data that is "fuzzy" and uncertain (i.e., relatively blurred).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, data type, network, user need, process, process step or steps, to the objective, spirit, scope of the present invention. All such modifications are intended to be within the scope of the claims appended hereto.

The invention claimed is:

1. A method of overlaying network diagram visualizations for visual interpretation by a user, said method comprising the steps of:
   displaying a first network diagram having nodes interconnected with links on a display device;
   overlaying at least one additional network diagram having at least one node that is the same as a node in the first network diagram, and wherein nodes and links of said at least one additional diagram are positioned in a corresponding manner to at least a portion of the nodes and links of the first diagram network;
   displaying only one of the first network diagram and at least one additional network diagrams in sharp definition; and
   blurring the remaining network diagrams and displaying said remaining network diagrams in a blurred state.

2. The method of claim 1, wherein at least said nodes of each said network diagram are color-coded, and wherein said nodes in said remaining network diagrams are displayed in color even after blurring.

3. The method of claim 1, further comprising decreasing the brightness of said remaining networks displayed in a blurred state, relative to a brightness of said network displayed in focus.

4. The method of claim 1, further comprising:
   selecting one of the network diagrams that are blurred;
   displaying the selected network diagram in sharp definition, and overlaying all other diagrams; and
   blurring the network diagram having been previously displayed in sharp definition.

5. The method of claim 1, further comprising skewing positions of said nodes of the remaining diagrams so that they do not exactly correspond to positions of the corresponding nodes in said network diagram in sharp definition, but under lap said nodes.

6. A display of overlaid network diagram visualizations for visual interpretation by a user, said display having been produced by:
   displaying a first network diagram having nodes interconnected with links on a display device;
   overlaying at least one additional network diagram having at least one node that is the same as a node in the first network diagram, and wherein nodes and links of said at least one additional diagram are positioned in a corresponding manner to at least a portion of the nodes and links of the first diagram network;
   displaying only one of the first network diagram and at least one additional network diagrams in sharp definition; and
   blurring the remaining network diagrams and displaying said remaining network diagrams in a blurred state.

7. The display of claim 6, wherein at least said nodes of each said network diagram are color-coded, and wherein said nodes in said remaining network diagrams are displayed in color even after blurring.

8. The display of claim 6, wherein said remaining networks displayed in a blurred state, are displayed with decreased brightness relative to a brightness of said network displayed in sharp definition.

9. The display of claim 6, wherein upon selection of one of the network diagrams that is displayed blurred, the selected network diagram is displayed in sharp definition, and overlaying all other diagrams; and the network diagram having been previously displayed in sharp definition is blurred.

10. The display of claim 6, wherein said nodes of the remaining diagrams are skewed so that they do not exactly correspond to positions of the corresponding nodes in said network diagram displayed in sharp definition, but under lap said nodes.

11. The display of claim 6, wherein upon selecting a portion of the network diagram displayed in sharp definition that defines interconnected nodes of interest; the nodes in the remainder of the sharp definition network diagram are blurred and displayed in a blurred state.

12. A computer readable medium carrying one or more sequences of instructions from a user of a computer system for visualizing one or more data sets, wherein execution of one or more sequences of instructions by one or more processors cause the one or more processors to perform the steps of:

displaying a first network diagram having nodes interconnected with links on a display device;

overlaying at least one additional network diagram having at least one node that is the same as a node in the first network diagram, and wherein nodes and links of said at least one additional diagram are positioned in a corresponding maimer to at least a portion of the nodes and links of the first diagram network;

displaying at least a portion of only one of the first network diagram and at least one additional network diagrams in sharp definition; and blurring the remaining network diagrams and displaying said remaining network diagrams in a blurred state.

13. A method of overlaying network diagram visualizations for visual interpretation by a user, said method comprising the steps of:

displaying a first network diagram having nodes interconnected with links on a display device;

overlaying at least one additional network diagram having nodes and links positioned in a corresponding manner to at least a portion of the nodes and links of the first diagram network;

displaying only one of the first network diagram and at least one additional network diagrams in sharp definition;

blurring the remaining network diagrams and displaying said remaining network diagrams in a blurred state; and skewing positions of said nodes of the remaining diagrams so that they do not exactly correspond to positions of the corresponding nodes in said network diagram in sharp definition, but under lap said nodes.

14. A method of overlaying network diagram visualizations for visual interpretation by a user, said method comprising the steps of:

displaying on a display device a first set of data on a network diagram having nodes interconnected with links;

overlaying at least one additional set of data on said network diagram wherein said at least one additional set of data includes data that corresponds to and overlays data from said first set on at least one node as displayed on said diagram;

displaying only one of the sets of data in sharp definition; and blurring the remaining sets of data and displaying said remaining sets of data in a blurred state.

15. The method of claim 14, wherein said sets of data are gene expression data.

* * * * *

UNITED STATES PATENT AND TRADEMARK OFFICE
CERTIFICATE OF CORRECTION

PATENT NO.        : 7,224,362 B2
APPLICATION NO.   : 10/356122
DATED             : May 29, 2007
INVENTOR(S)       : Kincaid et al.

Page 1 of 1

It is certified that error appears in the above-identified patent and that said Letters Patent is hereby corrected as shown below:

In the Title, delete "Visualization and" and insert --Visualizations of--, therefor.

In column 14, line 46, in Claim 8, delete "state," and insert -- state --, therefor.

In column 15, line 10, in Claim 12, delete "maimer" and insert -- manner --, therefor.

Signed and Sealed this

Fourth Day of December, 2007

JON W. DUDAS
*Director of the United States Patent and Trademark Office*